United States Patent
Corella

(10) Patent No.: US 6,169,203 B1
(45) Date of Patent: Jan. 2, 2001

(54) METHOD OF PREPARATION OF ALKALI-METAL AMIDES

(75) Inventor: Joseph A. Corella, Zelienople, PA (US)

(73) Assignee: Mine Safety Appliances Company, Pittsburgh, PA (US)

( * ) Notice: Under 35 U.S.C. 154(b), the term of this patent shall be extended for 0 days.

(21) Appl. No.: 09/028,890

(22) Filed: Feb. 24, 1998

(51) Int. Cl.⁷ .............................. C07C 209/00; C07F 7/10
(52) U.S. Cl. ..................... 564/2; 564/463; 556/412; 556/463; 556/466
(58) Field of Search ............... 564/2, 463; 556/412, 556/463, 466; 252/182.12

(56) References Cited

U.S. PATENT DOCUMENTS 4,595,779 * 1/1986 Morrrison et al. ..................... 564/2
5,493,038 * 2/1996 Hall et al. ............................. 564/2

* cited by examiner

*Primary Examiner*—Shailendra Kumar
(74) *Attorney, Agent, or Firm*—J. G. Uber, Esq.; H. E. Bartony, Jr., Esq.

(57) ABSTRACT

A method for synthesizing an alkali-metal amide comprises the step of charging a reactor vessel with a reaction mixture comprising an alkali metal selected from the group of lithium, sodium, potassium or cesium, an electron carrier, and a disubstituted amine. The disubstituted amine preferably has the formula $R^1R^2NH$, wherein $R^1$ and $R^2$ are independently, the same or different, an alkyl group or $-SiR^3$, wherein $R^3$ is an alkyl group, an aryl group, or an aryl group substituted with an alkyl group. The reaction to form the alkali-metal amide product occurs without the use of a solvent.

18 Claims, No Drawings

METHOD OF PREPARATION OF ALKALI-METAL AMIDES

FIELD OF THE INVENTION

The present invention relates to the preparation of alkali-metal amides and, particularly, to the preparation of lithium, sodium, potassium and cesium amides.

BACKGROUND OF THE INVENTION

Alkali metal alkylamides have been prepared directly from alkali metals under a number of synthetic routes. For example, lithium diisopropylamide (LDA) has been produced directly from lithium metal using an "electron carrier" or "hydrogen acceptor" such as styrene in THF as follows:

See U.S. Pat. No. 4,595,779. Suitable electron carriers are generally conjugated, unsaturated hydrocarbons. These electron carriers are noted to readily accept electrons from an alkali metal to form free radicals or carbanions.

Likewise, lithium alkylamides of the general formula $(R_3M)_xNLi(R^1)_y(LB)_z$, (wherein R and $R^1$ are $C_1$–$C_8$ alkyl, cycloalkyl or alkylene groups, LB is a Lewis base, x and y are integers having the sum of 2, and z is greater than 1) have been formed from reacting bulk lithium metal with an alkylamine in the presence of a solvent and certain electron carriers. See U.S. Pat. No. 5,493,038. The use of electron carriers in such reactions, however, often results in formation of undesirable byproducts which are very difficult to separate from the desired product.

International Patent Application No. PCT/US96/10923 discloses a process for preparing organometallic amides via a number of reaction schemes in the presence and absence of an electron carrier. However, each of those reactions requires the presence of a solvent. In such reactions, solvents takes up valuable reactor volume and often necessitate difficult separation procedures to arrive at a usable product.

A one-step synthesis of alkali-metal hexamethyldisilazanes without the use of an electron carrier has been developed by Chiu et al. See U.S. Pat. No. 5,420,322. Under this method, lithium, sodium or potassium is reacted with a 1,1,1,3,3,3-hexamethyldisilazane at a reaction temperature above the melting point of the alkali metal. Although, very pure product is obtained under the method of Chiu et al. without difficult separation procedures, relatively high temperatures and pressures are required (especially in the case of the synthesis of lithium hexamethyldisilazanes).

It is thus very desirable to develop alternative synthetic schemes for the production of alkali-metal alkylamides.

SUMMARY OF THE INVENTION

Generally, the present invention provides a method for synthesizing an alkali-metal amide composition comprising the following step:

charging a reactor vessel with a reaction mixture comprising an alkali metal selected from the group of lithium, sodium, potassium or cesium, an electron carrier, and a disubstituted amine. The reaction to form the alkali-metal amide product occurs without the use of a solvent.

The disubstituted amine has the formula $R^1R^2NH$, wherein $R^1$ and $R^2$ are preferably independently, the same or different, an alkyl group or —$SiR^3$, wherein $R^3$ is an alkyl group, an aryl group, or an aryl group substituted with an alkyl group. The reactants can be added in stoichiometric quantities without the addition of any solvent(s). Potentially difficult separations and potentially undesirable byproducts resulting from the presence of solvent(s) are thereby avoided. Furthermore, valuable reactor space is conserved.

The alkali-metal amide compositions of the present invention have the following general formula: $MNR^1R^2$, wherein M is an alkali metal selected from the group of lithium, sodium, potassium or cesium. Preferably, $R^1$ and $R^2$ are the same to form an alkali-metal amide composition of the general formula: $MN(R^1)_2$.

As used herein, the term "alkyl group" refers generally to normal, branched and cyclic alkyl groups. Preferably such alkyl groups are $C_1$–$C_{12}$ alkyl groups. More preferably, such alkyl groups are $C_1$–$C_6$ alkyl groups.

As used herein, the term "aryl group" refers generally to a phenyl group. Such phenyl groups may be substituted, for example, with one or more alkyl groups. Preferably, such alkyl groups substituents are $C_1$–$C_6$ alkyl groups. Preferred alkyl substituent groups include a methyl group, an ethyl group, an isopropyl group, an n-propyl, a t-butyl group and an n-butyl group.

Preferably, the reaction to form the alkali-metal amide product occurs at a temperature above the melting point of the alkali-metal amide product. In that regard, it is preferable to maintain the alkali-amide product in a liquid state to facilitate heat and mass transfer and to thereby facilitate a complete reaction. Maintenance of the alkali-amide product in a liquid state is not necessary, however. The reaction will proceed, for example, when the reaction mixture is a slurry. Indeed, many of the reactions of the present invention will proceed at temperatures as low as, for example, room temperature (that is, approximately 20° C.).

The reaction to form the alkali-metal amide will proceed regardless of the order of addition of the reagents. However, it is preferable to add the electron carrier last in the reaction to minimize initial pressure within the reactor as well as to minimize the potential for undesirable polymerization of the electron carrier. For example, in one reaction scheme, the reactor vessel is charged with the alkali metal and the disubstituted amine. The reaction vessel is preferably heated to a temperature above the melting point of the alkali-metal amide product either before or after addition of the alkali metal and the disubstituted amine. After charging the reactor vessel with the alkali metal and the alkylamine, the electron carrier is added to the reactor vessel. Alternatively, the reactor vessel can first be charged with the alkali metal, and a mixture of the disubstituted amine and the electron carrier can be added thereto.

Preferably, electron carriers that are converted to a byproduct having a boiling point below the decomposition temperature of the alkali-metal amide product are used in the present invention. Likewise, the electron carrier itself preferably has a boiling point below the decomposition temperature of the alkali-metal amide product. Such electron carriers and their corresponding byproducts are generally easily separable from the product via distillation. Preferably, the electron carriers and their corresponding byproducts have boiling points at least approximately 10° C. below the decomposition temperature of the alkali-metal amide product.

The electron carrier is preferably a conjugated hydrocarbon. More preferably, the electron carrier is a conjugated, aliphatic hydrocarbon. Most preferably, the electron carrier is isoprene. Although it is generally believed in the art that isoprene and other conjugated hydrocarbon electron carriers will polymerize at temperatures above 60° C. in the presence of an alkali metal (see, for example, Allcock, H. R. and Lanyse, F. W., *Contemporary Polymer Chemistry*, second edition, Prentice-Hall, Inc., p. 320 (1990)) and that a solvent is thus necessary to limit or prevent polymerization, it has been discovered that no polymerization of the electron carrier occurred under the reaction conditions of the present invention.

The reactions of the present invention can be carried out at relatively low pressures and temperatures. Moreover, the absence of a solvent greatly simplifies separation/purification of the alkali-metal amide to achieve a relatively high purity (for example, >99%) as compared to previous reaction schemes requiring the use of an electron carrier and an ethereal or hydrocarbon solvent. Increased reactor loading is also possible with the reactions of the present invention as compared to current reaction schemes for the production of alkali-metal amides in which solvent systems are required. Indeed, approximately 50 to 75% of reactor loading arising from the use of such solvent systems can be eliminated. Further, many of the reactions of the present invention provide substantially quantitative yields with relatively short reactions times (typically, less than one hour).

DETAILED DESCRIPTION OF THE INVENTION

In the reactions of the present invention, the reaction vessel may be charged with the alkali metal and a substituted or disubstitued alkylamine, preferably under an inert (for example, argon) atmosphere. The reaction vessel is preferably maintained above the melting point of the alkali-metal amide to be produced. An electron carrier (for example, isoprene) is then slowly added to the reaction vessel. Alternatively, the reaction can, for example, be initiated at ambient temperature and slowly allowed to reach a temperature above the melting point of the alkali-metal alkylamide product by the end of the electron carrier addition.

Upon addition of the electron carrier, a substantially immediate increase in temperature was observed in the experiments of the present invention indicating a substantially instantaneous reaction. After addition of the electron carrier was completed, the reaction was preferably stirred for approximately one hour. Substantially quantitative yields (for example, >99%) were observed in a number of experiments.

EXAMPLE 1

In one reaction to produce lithium hexamethyldisilazane, Li metal (1 mole) and hexamethyldisilazane (HMDS) (1 mole) were charged to a reaction vessel under an argon atmosphere according to the following general reaction formula:

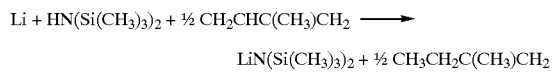

$$Li + HN(Si(CH_3)_3)_2 + \tfrac{1}{2} CH_2CHC(CH_3)CH_2 \longrightarrow$$
$$LiN(Si(CH_3)_3)_2 + \tfrac{1}{2} CH_3CH_2C(CH_3)CH_2$$

The reaction vessel was heated to approximately 90 to 95° C., which is above the melting temperature of the lithium hexamethyldisilazane product. Isoprene (0.5 mole) was then slowly added to the Li/HMDS mixture. An immediate exotherm was observed. After addition of the isoprene was complete, the reaction was stirred for an additional hour.

The 2-methylbutene byproduct was distilled off at approximately 90° C. A substantially quantitative yield (that is, >99%) was observed. The purity of the lithium hexamethyldisilazane product was in excess of 99%. The lithium hexamethyldisilazane product can be isolated as a pure solid or diluted in an etherial, aromatic, or aliphatic hydrocarbon solvent.

EXAMPLE 2

In another experiment 0.5 mole of α-methylstyrene (AMS) was added to a stirred mixture of lithium and HMDS over a period of approximately one hour at approximately 100 to 115° C. A yield of approximately 50 to 60% was observed.

EXAMPLE 3

AMS (0.75 mole) was added to a stirred mixture of lithium and HMDS over a 35 minute period. Color changes and the reduced size of the lithium metal indicated occurrence of a reaction. The addition of tetrahydrofuran (THF) after overnight heating was investigated to study whether the reaction would proceed to completion. Upon addition of the THF, the reaction went to 80 to 85% completion.

EXAMPLE 4

A reactor was charged with 1 mole of lithium and 0.5 moles of isoprene and heated to approximately 75 to 85° C. HMDS was added slowly over a period of approximately two hours. Increased reactor pressure and consumption of lithium metal indicated formation of LiHMDS. The reaction was nearly quantitative.

EXAMPLE 5

A reactor was charged with 1 mole of lithium and 0.5 moles of AMS and heated to approximately 75 to 85° C. HMDS was added slowly over a period of approximately one hour. The reactor was heated to approximately 92° C. for several hours. As calculated from the lithium metal recovered, the yield was approximately 77%.

EXAMPLE 6

A reactor was charged with 1 mole of potassium metal and 1 mole of HMDS. Isoprene was added over an approximately two hour period. The reactor was maintained at a temperature of approximately 95 to 112° C. During the addition of isoprene (0.5 moles), heat was evolved and maintained by adjusting the addition rate. As the reaction continued and the formation of potassium hexamethydisilazane was evident, the reaction mixture became thick and ceased to stir. In that regard, the temperature within the reactor was below the melting point of the potassium hexamethydisilazane product. The reaction proceeded to 90 to 95% completion before loss of mobility.

EXAMPLE 7

A reactor was charged with 1.0 mole of lithium metal and 1.0 mole of di-isopropylamine were charged to a reactor. Over a 2.5 hour period, 0.5 moles of isoprene were added. The reaction temperature ranged from approximately 21 to 45° C. over the addition of isoprene. The reaction proceeded best at temperature over 40° C. The reaction mixture became thick as the reaction proceeded. The reaction proceeded to greater than 90% completion Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method for synthesizing an alkali-metal amide product comprising the step comprising the steps of:
   charging a reactor vessel with a reaction mixture comprising an alkali metal selected from the group of lithium, sodium, potassium or cesium, an electron carrier and a disubstituted amine; the reaction to form the alkali-metal amide occurring without the use of a solvent.

2. The method of claim 1 wherein the disubstituted amine has the formula $R^1R^2NH$, wherein $R^1$ and $R^2$ are independently, the same or different, an alkyl group or —$SiR^3$, wherein $R^3$ is an alkyl group, an aryl group, or an aryl group substituted with an alkyl group.

3. The method of claim 1 wherein the reaction is carried out at a temperature above the melting point of the alkali-metal amide product.

4. The method of claim 2 wherein $R^1$ and $R^2$ are independently a $C_1$–$C_{12}$ alkyl group.

5. The method of claim 2 wherein $R^1$ and $R^2$ are independently a $C_1$–$C_6$ alkyl group.

6. The method of claim 2 wherein $R^3$ is a phenyl group or a phenyl group substituted with a $C_1$–$C_6$ alkyl group.

7. The method of claim 2 wherein the phenyl group is substituted with a methyl group, an ethyl group, an isopropyl group, an n-propyl, a t-butyl group or an n-butyl group.

8. The method of claim 1 wherein the alkali metal is lithium.

9. The method of claim 1 wherein the alkali metal is potassium.

10. The method of claim 1 wherein the electron carrier is added to the reactor vessel after charging the reactor vessel with the alkali metal and the disubstituted amine.

11. The method of claim 1 wherein a mixture of the disubstituted amine and the electron carrier is added to the reactor vessel after charging the reactor vessel with the alkali metal.

12. The method of claim 1 wherein the disubstituted amine is hexamethyldisilazane.

13. The method of claim 1 wherein the substituted amine is di-isopropylamine.

14. The method of claim 1 wherein the electron carrier has a boiling point at least approximately 10° C. below the decomposition temperature of the alkali-metal amide and the electron carrier is converted in the reaction to a byproduct having a boiling point at least approximately 10° C. below the decomposition temperature of the alkali-metal amide.

15. The method of claim 1 wherein the electron carrier is isoprene.

16. The method of claim 1 wherein the electron carrier is α-methylstyrene.

17. The method of claim 3 wherein the reactor vessel is heated to a temperature above the melting point of the alkali-metal alkylamide before addition of the electron carrier.

18. The method of claim 3 wherein the reactor vessel is heated to a temperature above the melting point of the alkali-metal alkylamide during addition of the electron carrier.

* * * * *